(12) United States Patent
Hughes et al.

(10) Patent No.: US 11,872,109 B1
(45) Date of Patent: Jan. 16, 2024

(54) CUSTOMIZED EAR COMPRESSION DEVICE FOR KELOID MANAGEMENT

(71) Applicants: Lowell Hughes, The Valley (AI); Anthony Lee Delligner, Burlington, NC (US); Melinda K. M. Goddard, The Valley (AI); Terry E. Brady, The Valley (AI)

(72) Inventors: Lowell Hughes, The Valley (AI); Anthony Lee Delligner, Burlington, NC (US); Melinda K. M. Goddard, The Valley (AI); Terry E. Brady, The Valley (AI)

( * ) Notice: Subject to any disclaimer, the term of this patent is extended or adjusted under 35 U.S.C. 154(b) by 0 days.

(21) Appl. No.: 18/237,019

(22) Filed: Aug. 23, 2023

(51) Int. Cl.
*A61F 5/01* (2006.01)
*A61F 11/00* (2022.01)

(52) U.S. Cl.
CPC ............ *A61F 11/00* (2013.01); *A61F 5/01* (2013.01)

(58) Field of Classification Search
CPC ...... A61F 11/00; A61F 11/202; A61F 11/006; A61F 11/04; A61F 11/045; A61F 11/06; A61F 11/08; A61F 11/14; A61F 11/085; A61F 11/10; A61F 11/12; A61F 11/20; A61F 11/145; A61F 2240/002; A61F 2240/005; A61F 2240/004
See application file for complete search history.

(56) References Cited

U.S. PATENT DOCUMENTS

2021/0282974 A1* 9/2021 Zopf .................. A61F 5/05891

OTHER PUBLICATIONS

Cleveland Clinic, Keloid on Ear. Management and Treatment. Last Reviewed by Cleveland Clinical Medical Professional on Aug. 22, 2022. Accessed from: https://my.clevelandclinic.org/health/diseases/24047-keloid-on-ear. (citation for methods of treatment).
Elsaie ML. Update on management of keloid and hypertrophic scars: a systemic review. Journal of Cosmetic Dermatology. 2021; 20: 2729-2738.
Lane JE, Waller JL. and Davis LS, Relationship between age of ear piercing and keloid formation. Pediatrics. 2005. 115(5), pp. 1312-1314.

(Continued)

*Primary Examiner* — Majid Jamialahmadi

(57) ABSTRACT

The present innovation is a customized compression device for prevention and treatment of keloids and hypertrophic scarring, primarily a frequent complication of ear piercing. The "one size fits all" design of traditional devices can compromise efficacy due to uneven fit and compression. This invention harnesses 3D digital scanning to capture the intricate contours of the ear for every patient, for personalized compression therapy. Using 3D printing, shells are fabricated with biocompatible materials such as Polylactic Acid, shape memory polymers, or silicone-based substances. In primary embodiments, device functionality is achieved with compression clips or spring-open, single-piece structures. The custom fit, potential for infusion of therapeutic agents (e.g., corticosteroids), and engineered porosity combine to improve keloid management from uniform pressure distribution and optimal healing. Additionally, the 'shells' can be pigmented to match patient skin tones and encourage compliance. The invention thus offers tailored keloid treatment, as well as prevention for high-risk individuals.

8 Claims, 5 Drawing Sheets

(56) References Cited

OTHER PUBLICATIONS

McGinty S and Siddiqui WJ. Keloid.[Updated Jul. 24, 2021]. StatPearls [Internet]. 2022. Treasure Island (FL): StatPearls Publishing.

Nangole FW and Agak GW. Keloid pathophysiology: fibroblast or inflammatory disorders?. Journal of Plastic, Reconstructive, and Aesthetic Surgery. 2019.22, pp. 44-54.

\* cited by examiner

CUSTOMIZED EAR COMPRESSION DEVICE FOR KELOID MANAGEMENT

FIELD OF THE INVENTION

The present invention relates to the field of dermatology and reconstructive surgery, specifically the prevention and management of keloid or hypertrophic scar formation. Although keloids can form as a result of cuts, burns, tattoos, acne, insect bites, and rashes such as chickenpox, they are particularly common following ear piercing. In one study, up to half of the individuals began to form keloid tissue between three and twelve months after ear piercing, with the likelihood of formation in up to 80% of those aged 11 years or older, with a 23.5% likelihood for younger individuals (Lane et al, 2005). While surgery is the most specific and immediate approach, secondary keloids often form as a result of excision of the primary keloids, as well as other methods. As earlobe piercing is especially popular, and as the practice appears be an enduring aspect of many cultures, an effective post-surgical device could resolve and prevent keloid recurrence, thereby avoiding the public health costs and patient impact from less reliable alternatives. The invention encompasses a unique method and associated devices for optimizing compression therapy pre- and post-keloid removal. Using 3-D digital scanning technology, the invention produces an individualized compression device that matches the contours of each patient's earlobe or other external ear anatomy. Through this customized, precision approach, the invention would advance the effectiveness of compression therapy, ensure consistent pressure distribution, and thus reduce the recurrence rates and severity of keloids and hypertrophic scarring.

BACKGROUND OF THE INVENTION

The skin is a vital and multifaceted organ, the largest of the human body. Skin plays a critical role in protection against external factors, with a primary function as the defensive barrier against environmental threats (e.g., pathogens, pollutants, UV radiation and physical forces). Given its surface area and exposure, the skin is invariably prone to various kinds of damage, whether from accidental trauma, surgical procedures, thermal burns, or other causes. When cutaneous injury occurs, a lengthy healing process involving a cascade of responses is initiated, which can lead to the formation of scars.

Essential for survival, the complex interplay of cellular and biochemical events in wound healing can thus lead to three predominant outcomes characterized by distinct pathophysiological mechanisms. First, the formation of a mature scar, which represents an organized meshwork of collagen fibers and cells, signifying successful tissue repair and remodeling. Second, aberrant wound healing, leading to excessive collagen synthesis and a pathological proliferation of fibroblasts. This can manifest as hypertrophic scars, which remain within the original boundaries of the wound, or they can form a challenging subset of scars, or keloids, which not only replace lost or damaged skin but can also extend beyond the original wound site. In certain circumstances exacerbated by factors such as prolonged inflammation, infection, or impaired blood supply, the injury may also fail to progress through normal stages of healing. This stagnation can result in the development of chronic wounds or ulcers, which require specialized intervention for resolution.

Wound healing is a multifaceted process that begins with an inflammatory response, where the body eliminates damaged tissues and contaminants. Following this, the proliferative phase is marked by increased fibroblast activity, extracellular matrix synthesis, and collagen deposition. Overactive fibroblasts resulting from skin trauma can produce excessive collagen and lead to anomalies like the formation of keloids during this phase. This healing cascade concludes with the skin remodeling stage, where collagen realigns, and the scar matures. In addition to fibroblasts, macrophages have been shown to play a role in this process. Importantly, M2 macrophage cells promote tissue repair and are released in response to skin damage. M2 cells secrete anti-inflammatory cytokines, interleukin-2 and tissue growth factor beta (IL-2 and TGF-B, respectively), the latter of which have been correlated to keloid formation (Nangole & Agak, 2019).

Mechanical dynamics, like compression therapy, can also impact how tissues react to trauma. The skin consists of several layers, beginning with the outermost stratum corneum, followed by the stratum lucidum, stratum *granulosum*, stratum *spinosum*, and the stratum basale. The use of compression forces of stress, strain, or a combination thereof at a target site can thus modulate the mechanical environment around a wound site with respect to keloid (or scar) formation and progression. Overall pressures can be dynamic (oscillating) and/or constant, functioning to reduce stresses below an undamaged region to promote healing, as well as decrease the potential for emergence or recurrence of keloids or hypertrophic scars. The effects of compression in healing have been anecdotally observed when regularly worn garments exert pressure on specific parts of a surgical scar, such as a belted waistline. As such, areas of the scar under consistent pressure often heal more optimally than those where the style or cut of the clothing fits more loosely.

Mechanistically, compression is believed to reduce blood flow to the keloid, thereby limiting the supply of nutrients to the scar tissue, which can directly inhibit growth. The pressure from compression also appears to modify the activity of the fibroblasts, leading to reduced collagen synthesis. However, with respect to this frequent ear-piercing sequelae, the earlobe distinct and intricate structure, combined with individual variability, makes compression strategies especially challenging for treating keloid cases. Most compression devices follow a generic design, or "one-size-fits-all" approach that does not conform to the patient's specific earlobe geometry. Ear anatomy is especially individualistic as compared to most other human features with greater shape similarities (e.g., head shapes, limbs, noses and lips).

Keloids, often described as "rubbery nodules," can be disfiguring, tender and/or irritating, and earlobe keloids are among the most common cases that present as complications from the practice of ear piercing. Other risk factors include genetic predisposition, with greater prevalence in African, Hispanic, and Asian populations, which are considered more susceptible to keloid and hypertrophic scar formation. While the exact causes in certain groups versus others have not been fully characterized, there is an apparent link to skin pigmentation. A greater incidence of keloid development during pregnancy and puberty has also been observed, with some genetic conditions (e.g., Rubinstein-Teybi & Goeminne syndrome) further increasing the risk (McGinty & Siddiqui, 2022). Prevention of formation, or a means to mitigate their progression in high-risk cases, could address up to 11 million keloid cases that develop annually from an estimated 100 million scars from elective and trauma-related surgeries, worldwide (Elsaie, 2021).

In comparison to hypertrophic scars, keloids are biologically and developmentally distinct. Keloids are a manifestation of abnormal wound healing and are distinguished by their unusually high rates of cellular growth and low apoptosis rates. Collagen synthesis in keloids has been found to be up to 20 times greater than in normal skin and 3 times greater than in hypertrophic scars (McGinty & Siddiqui, 2022). The formation of keloids is thought to be triggered particularly by platelet growth factors, which induce fibroblast chemotaxis at the trauma site, leading to collagen overproduction. Keloids may also form due to a sustained inflammatory response resulting from prolonged cytokine release that stimulates fibroblast proliferation and subsequent deposition in the extracellular matrix (Nangole & Agak, 2019).

Unlike typical scars, keloids exhibit an aggressive healing response. While hypertrophic scars remain confined to the original wound margins, keloids are typically more invasive and may compromise adjacent healthy tissue. That is, rather than "patching" the damaged region of the skin, keloids may grow beyond the defined boundaries of the initial wound.

Beyond the aesthetics associated with keloid overgrowth, these raised and discolored regions are often painful or itchy. They can also lead to functional limitations and restrict movement, especially when located near joints. While not typically a cause for serious health concerns, the discomfort and stress associated with their notably abnormal appearance, and occasionally more deleterious effects, bring many patients to seek treatment for keloid scars.

Clinical management of hypertrophic scars and keloids on the earlobe and external ear include surgical and non-surgical methods. Current methods include chemotherapy, cryotherapy, laser therapy, ligature, radiation, steroid injections, surgery, or "pressure earring" treatment (Cleveland Clinic, 2022). Surgical procedures typically involve excision and reconstruction of the tissues. However, without adjunctive therapy, there is a significant potential for post-surgical recurrence that can be more extensive than the initially excised tissues. This tendency to keloid proliferation, combined with potential for recurrence and resistance to various treatments, present considerable treatment issues. Thus, dermatologists, surgeons and general practitioners have continued to seek effective and lasting solutions to address the persistent problem of keloids.

In fact, using compression both pre- and post-surgically has demonstrated a reduction in keloid recurrence rates and severity. However, clinicians often find themselves limited in options when choosing suitable earlobe devices. Many commercially available devices are ill-fitted in size and shape for post-operative compression. Sometimes called, "pressure earrings," the generic approach has obvious healing shortcomings, because these devices do not precisely conform to patient tissue contours. This can result in uneven pressure distribution and lead to inadequate or inconsistent compression. Similarly, poorly fitting devices are often uncomfortable, which can negatively impact compliance with respect to the recommended duration of therapy. Notably, compression therapy can sometimes result in pressure sores as such the duration of compression device application at the target region can vary between individuals and may range from short periods (weeks) to extended periods (months). In most cases, a compression device would provide the greatest efficacy when applied from the inflammatory and proliferative stages of wound recovery and throughout the skin remodeling phase.

Thus, while compression therapy is beneficial for keloid and hypertrophic tissue management, optimally designed devices are not currently available to provide consistent scar mitigation and user comfort. This proposed invention leverages the capabilities of 3-D digital scanning to meticulously map, cast, customize and fabricate effective, comfortable compression therapy devices for reconstructed earlobes or other external ear sections as post-surgical adjunctive therapy and for prevention in high-risk individuals undergoing surgical procedures or ear piercing.

SUMMARY OF THE INVENTION

Described herein are devices, bandages, kits, and methods specifically designed to prevent or mitigate the formation of keloids and hypertrophic scars, particularly on the earlobe or other external ear sections, following surgical excision or other forms of trauma, including ear piercing. Methods for enhancing the healing of reconstructed earlobes or external ear segments and reducing keloid and hypertrophic scar formation are detailed. Generally, these devices are customized using 3-D digital scanning technology, allowing them to be securely and yet removably fitted onto the skin contours near the wound or surgical site. These devices are engineered to protect the wound from both internal (i.e., dermal) and external (i.e., physiological) stresses. By ensuring consistent, even pressure distribution on the wound through the individualized design, the devices aim to enhance compression therapy in reducing keloid and hypertrophic scar recurrence and severity. Such outcomes may be further enhanced by infusion of therapeutic agents, as well as aesthetic features to encourage compliance that may be required over extended treatment periods.

In the primary embodiments, the devices are crafted using advanced 3-D digital scanning, precisely capturing the contours of reconstructed earlobes or any other part of the external ear. This meticulous mapping allows for the design of a digital cast prototype of the affected region. This cast is then expanded uniformly, providing space for a supple lining like a thin silastic sheet. The digitally optimized data is then processed to produce compression 'shells', which are subsequently fabricated using a 3-D printer.

In the primary embodiment, 'shells' are primarily fabricated using Polylactic Acid (PLA), a biodegradable and bioactive thermoplastic aliphatic polyester to ensure biocompatibility and adaptability. Alternative materials may include shape memory polymers, which have the unique ability to return from a deformed state to their original and permanent shape when exposed to an appropriate stimulus for increased pressure application, as well as silicone-based materials often employed in medical applications due to high biocompatibility, flexibility, and durability. The 3D printing of these materials is capable of forming complex shapes and structures to conform to target regions, such as the ear. However, many polymeric materials, including inexpensive styrene matter, or a vast array of plastics, may also be used.

For added functionality in the primary embodiment, the 'shells' may be coupled with a compression clip device, facilitating the union of the two halves and ensuring both the desired compression intensity on the reconstructed area and a stable fit for efficacy, as well as compliance. In a second embodiment, a single-piece shell design would be engineered to spring open for a slide-on fit onto the earlobe or any external ear segment. These designs leverage the unique properties of thermoplastic, or shape memory polymers, which can be programmed to change shape in response to external stimuli to achieve shell designs with enhanced adaptability to individual ear contours. This customization thus ensures optimal compression to accelerate healing of the reconstructed area. In some embodiments, a biocompatible adhesive, such as polyacrylate-based or silicone-based pressure-sensitive adhesives, can be applied for further adherence.

Portions of these devices may be more or less porous, allowing for airflow as appropriate for the patient and site. Likewise, the outer shells can be transparent or specially pigmented. In addition to matching precise contours of the region, 3D-printed capabilities would enable infusion with customized pigments to match individual skin tone to visually blend with the individual's complexion. As such, minimizing device prominence would foster patient compliance by enhancing self-confidence while using the device for the prescribed treatment duration.

Optional embodiments of the compression devices may also incorporate therapeutic agents, such as corticosteroids. These agents can assist in various phases of the wound healing process. For instance, the embedded agent could be a medicinal compound, a growth factor protein, essential vitamins, or a blend thereof. The custom designed and 3D-printed shells can thus be configured to deliver and release multiple active agents, optimizing and extending the healing and scar prevention process beyond compression.

This proposed invention establishes a transformative approach to managing earlobe and ear helical keloids, as well as hypertrophic scarring. The 3D-printed compression shells are tailored to the individual's unique ear contours, allowing for custom-fitted treatments suitable for any part of the pinna. Likewise, the devices could be employed preemptively and during the early stages of hypertrophic scarring, potentially decreasing the need for surgical interventions. Moreover, for those identified with a heightened predisposition to keloid and hypertrophic scar development, proactive applications of these personalized devices would offer an effective preventative measure if employed immediately following ear piercing, as well as keloid excision surgery.

BRIEF DESCRIPTION OF THE DRAWINGS

In the drawings, similar reference characters denote corresponding features consistently throughout the figures. The drawings are intended to depict exemplary embodiments of the invention and should not be construed to limit the scope of the patent.

DETAILED DESCRIPTION OF THE INVENTION

Figure 1A:
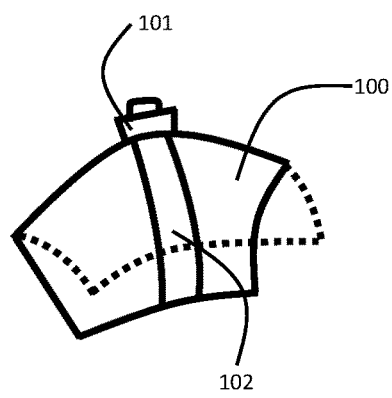
FIG. 1A is a front view of the compression shell and clip device, illustrating its general configuration and primary features as seen from the front perspective.

The compression device described herein is engineered to reduce the formation of keloids and other scar types. The device of the invention is customized to align and match with the distinct characteristics, contours, shapes, wound size and geometries of an individual's earlobe or other external ear parts. Embodiments of the present invention are adaptable to accommodate various wound dimensions and skin thicknesses, increasing applicability beyond the ear and would be suitable for diverse body regions. Beyond compression and customization features, the device material offers several modifications: the compression device can be (1) transparent, enabling real-time monitoring of the healing process, (2) tinted to match the skin tone of the patient, (3) designed with porosity to facilitate oxygen and fluid exchange or to deliver therapeutic agents, or (4) a blend of these properties. Such versatility ensures the device biocompatibility and discreetness, facilitating effective and novel clinical care for keloid and scar management across all skin types, age groups, ethnicities and body areas.

A critical aspect of the compression device in the present invention is associated with precision matching of the shape and contour at the patient application site. In the primary embodiment of the present invention, the target site, earlobe or other external ear section(s) of the patient ear is subjected to 3-dimensional digital scan that captures the contours, shapes, and geometries of the target site and forms a precise digital blueprint of the area, particularly in areas of complex anatomy and architecture, i.e., the ear region, capturing an accurate image is critical. To facilitate such imaging of the target region for the proposed compression device, advanced handheld high quality imaging capture software is utilized. By example, Scandy Pro™, which integrates with next generation smart phones, specializes in creating high-quality 3D scans using mobile device, built-in cameras. These software and image rendering programs have high-resolution capture and depth-sensing capabilities.

In the primary embodiment, the scanning software generates a comprehensive 3D representation of the patient target area for the compression device by capturing the ear from multiple angles, ensuring that the intricate curves, depths, and ridges are accurately represented. The software is designed to turn depth-sensing mobile devices into 3D scanners using an algorithm that stitches together the multiple scans to articulate every ridge, curve, and depth of the topography of the target region. Such capabilities include resolution and accuracy down to fractions of a millimeter, imparted by the advanced software algorithms that combine multiple scans for a comprehensive 3D image.

Once the image is acquired, the software editing tools can refine the scan, eliminating anomalies or imperfections. The precise nature of this 3D scan ensures that the subsequently 3D-printed compression device will align perfectly with each patient's unique ear contours. This would ensure maximum efficacy for keloid or scar mitigation as well as ensure optimal comfort. After scanning, a digital cast prototype of the affected area is created based on the scan data. This prototype can then be uniformly expanded digitally to account for the incorporation of a soft lining, such as a thin silastic sheet. This expansion thus ensures that the finalized device provides optimal compression without discomfort.

In one aspect of the present invention, the accuracy of 3D printing technology and the versatility of advanced materials enables precision transformation of the digital renderings of patient ear topography into customized and tailored compression shells. In a primary embodiment of this invention Polylactic Acid (PLA) is used as the printing material. The properties of PLA make for an exemplary material for contact compression devices. PLA is biodegradable, bioactive and non-toxic making the material particularly suitable for prolonged skin contact. Given the safety profile, PLA has become a preferred material for many medical applications requiring a direct patient interface.

In another embodiment, shape memory polymers (SMPs) represent an ideal material for the 3D printing of medical devices. These polymers can be temporarily deformed and later revert to their initial shape upon exposure to specific triggers, like temperature changes. SMP distinctive characteristics are particularly suitable for the custom-fit compression device of the present invention and ensure precise adaptability and alignment with the intricate contours of the ear anatomy.

In other embodiments, various materials are considered based on their unique characteristics tailored to the device requirements. Silicone-based materials, known for their flexibility, biocompatibility, and durability, offer patients a comfortable, smooth texture, typically desired in medical applications. Thermoplastic polyurethane (TPU), an elastomeric blend of hard plastic and soft silicone, features flexibility, abrasion resistance, and customizable firmness levels, which are essential when prioritizing comfort and precision fit. Acrylonitrile butadiene styrene (ABS), a sturdy plastic with impressive temperature resilience, is another candidate for 3D printing. While its durability can complement device compression, individual biocompatibility evaluations are crucial, especially for long-term skin contact. Additionally, Polyethylene terephthalate glycol (PETG) merges PLA user-friendliness with the enhanced durability typical of plastics, and its resistance to chemicals and UV light is noteworthy. Given PETG high clarity, it notably stands out as an optimal choice for transparent applications when real-time wound analysis is indicated.

In yet other embodiments of the present invention, further customization for aesthetic and functional needs can be achieved with these materials. By example, pigment can be added to PLA, TPU, or PETG. Thus, infusion of pigments in the advanced shell material can precisely match the patient skin tones, ensuring device discreetness and thereby enhancing compliance. Likewise, a transparent version allows for real-time monitoring of the healing process and may offer comparable cosmetic benefits depending on the stage or severity of the initial wound.

For all embodiments, 3D printing techniques allow for the customized compression device to be structured with microporosity to promote air and fluid exchange. Such parameters can be effectively engineered using SMPs or TPU, given their flexible properties. Porosity in the shell design would facilitate oxygen and moisture regulation, as well as serve as a conduit for delivery of therapeutics (e.g., corticosteroids). Incorporating such materials and features into the 3D printing process could thus broaden the scope the compression device with a balance of strength, adaptability, aesthetics, and biocompatibility, while fostering wound healing.

Figure 1B:
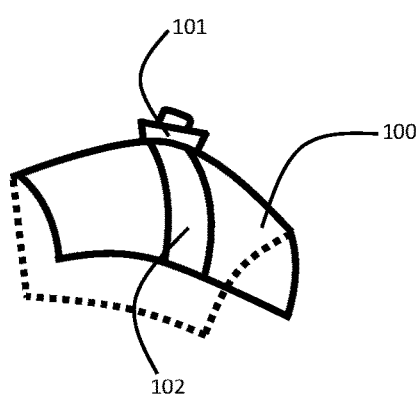
FIG. 1B depicts the back view of the compression shell and clip device, showing elements and features on the rear aspect of the device, which may not be visible or apparent from the front view.
Figure 1C:
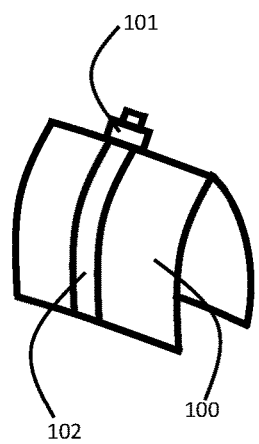
FIG. 1C provides a side view of the compression shell and clip device, highlighting the thickness, contouring, and other lateral features of the device that are essential for visualizing its three-dimensional structure.
Figure 2:
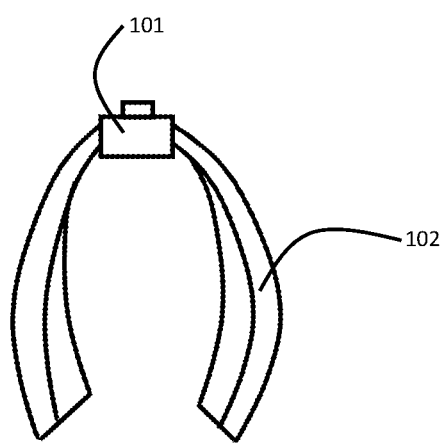
FIG. 2 provides a view of the clip device for the compression shell.
Figure 3A:
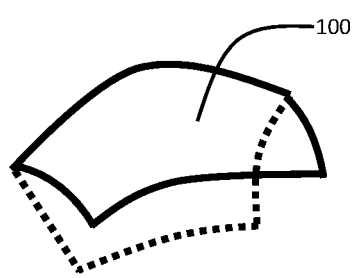
FIG. 3A depicts the front view of the slide-on, single-piece compression shell, illustrating its general configuration and primary features as seen from the front perspective.
Figure 3B:
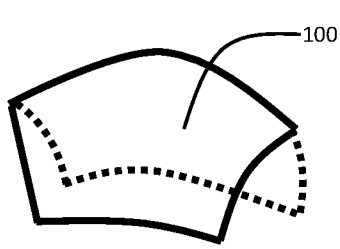
FIG. 3B provides a back view of the slide-on, single-piece compression shell, showing elements and features on the rear aspect of the device, which may not be visible or apparent from the front view.
Figure 3C:
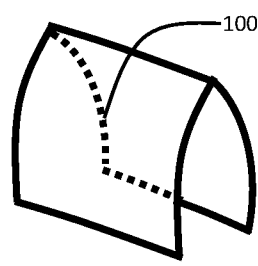
FIG. 3C provides a side view of the slide-on, single-piece compression shell, highlighting the thickness, contouring, and other lateral features of the device that are essential for visualizing its three-dimensional structure.
Figure 4A:
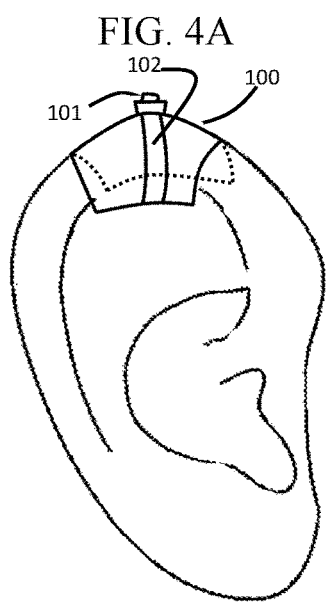
FIG. 4A depicts the compression device positioned on the helix of the ear, showing its fit and compatibility with this upper curved structure. The illustration provides insight into how the device conforms to the unique curvatures of the helix, ensuring optimal compression and user comfort.
Figure 4B:
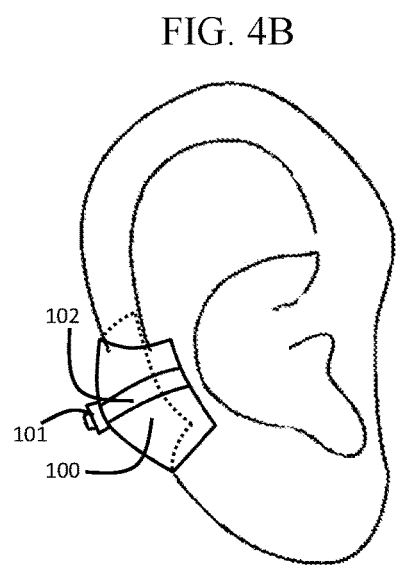
FIG. 4B displays the compression device attached to the anti-helix of the ear. The image reveals the device adaptability to this specific inner curved region, emphasizing its precision in alignment and the ability to target varying anatomical features of the ear.
Figure 4C:
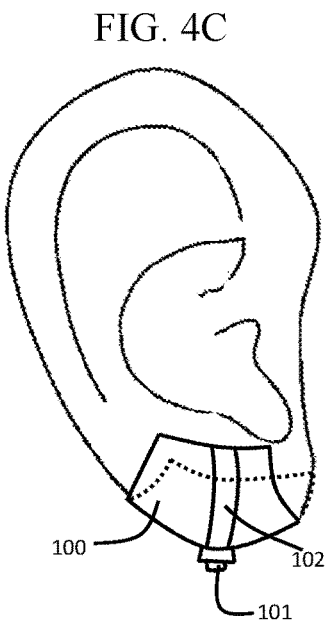
FIG. 4C illustrates the compression device affixed to the lobe of the ear. This representation demonstrates the device versatility in addressing lower ear regions, showing how its design can adapt to myriad ear anatomies for effective compression and therapeutic intervention.
Figure 5:
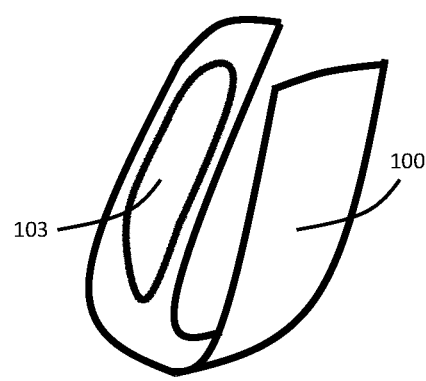
FIG. 5 presents the compression device enhanced with an inner silicone lining. This depiction highlights the added layer of the silicone for comfort and protection, ensuring a supple interface with the skin while maintaining the primary function of compression.

To provide requisite pressure to the target region, two or more mechanisms are used. (1) In FIGS. 1A-C and, a compression clip device 102 assists in joining the two halves of the compression shell 100, to ensure that the desired compression intensity is achieved and maintained on the reconstructed area. The compression clip device can be opened using a pressure release button 101 located on the device shell. (2) Alternatively, in FIGS. 3A-C, a single-piece shell 100 is engineered to spring open, allowing for a slide-on fit onto the earlobe, as shown in FIG. 4C, or other external ear parts, as shown in FIGS. 4A and 4B, and would allow for a smoother appearance. Finally, the compression device can be further enhanced with an inner silicone lining 103, as shown FIG. 5. This depiction highlights the added layer of silicone for comfort and protection, ensuring a supple interface with the skin while maintaining the primary device function of compression.

While the devices described herein offer illustrations and examples, these are included for clarity and cannot be construed to limit the scope or specifics of the invention. That is, the present invention centers on a customizable compression device engineered to counteract keloids and hypertrophic scars. The compression device design begins with a precise 3D-digital scan of the target area to capture its unique intricacies. The collected data is transformed into a comprehensive 3D representation to ensure a custom fit when the device is fabricated using 3D printing for effective scar mitigation and patient comfort. It would be obvious to anyone skilled in these arts that the compression device and customized form fitting could be adapted for various body parts, beyond that of the discussed embodiments associated with ear and earlobe anatomy, where keloids commonly manifest. Those skilled in the techniques employed for this invention would also understand that adjustments can be made without straying from the central themes of the claims.

What is claimed:

1. A method configured to treat and counteract a formation of keloids and hypertrophic scars comprising:
   a. conducting a 3-dimensional digital scan of an ear region to capture its contours, shapes, and geometries;
   b. using software and imaging programs with high-resolution capture and depth-sensing capabilities to produce a 3D representation image;
   c. digitally refining the 3D representation image to eliminate anomalies;
   d. creating a digital cast prototype based on the refined 3D representation image; and
   e. using 3D printing technology to transform the digital cast prototype into a customized compression device; wherein said customized compression device comprises:

a compression clip for assisting in joining two halves of said customized compression device, and a pressure release button located on said customized compression device for opening the compression clip;

wherein said customized compression device is custom-designed to match distinct characteristics, contours, shapes, wound size, and geometries of an individual's ear lobe or other external ear parts to treat and counteract the formation of keloids and hypertrophic scars.

2. The method of claim 1, wherein the customized compression device is adaptable to various wound dimensions and skin thicknesses.

3. The method of claim 1, wherein the customized compression device further comprising one or more of the following features:

a. being transparent for real-time monitoring of healing;
b. having a tint matching a skin tone of a patient;
c. possessing porosity to enable oxygen and fluid exchange;
d. possessing porosity to enable infusion and delivery of therapeutic agent(s).

4. The method of claim 1, wherein the 3-dimensional digital scan uses depth-sensing mobile devices converted into 3D scanners with algorithms that stitch together multiple scans.

5. The method of claim 1, wherein a 3D printing material for the 3D printing technology comprises one or more of: Polylactic Acid (PLA), shape memory polymers (SMPs), silicone-based materials, thermoplastic polyurethane (TPU), acrylonitrile butadiene styrene (ABS), or Polyethylene terephthalate glycol (PETG).

6. The method of claim 1, wherein the customized compression device is structured with micro-porosity to promote air and fluid exchange, wherein the porosity facilitates oxygen and moisture regulation or serves as a conduit for delivery of therapeutic agents.

7. The method of claim 1, wherein the customized compression device is further enhanced with an inner lining, ensuring an interface with a skin while maintaining its primary compression function.

8. The method of claim 1, wherein the customized compression device further comprises pigments that match an individual's skin tones or is transparent.

* * * * *